(12) United States Patent
Goerlitz-Jessen (10) Patent No.: US 11,771,453 B2
(45) Date of Patent: Oct. 3, 2023

(54) FORCEPS

(71) Applicant: Duke University, Durham, NC (US)

(72) Inventor: Mark Goerlitz-Jessen, Durham, NC (US)

(73) Assignee: Duke University

( * ) Notice: Subject to any disclaimer, the term of this patent is extended or adjusted under 35 U.S.C. 154(b) by 139 days.

(21) Appl. No.: 17/356,160

(22) Filed: Jun. 23, 2021

(65) Prior Publication Data

US 2021/0393283 A1 Dec. 23, 2021

Related U.S. Application Data

(60) Provisional application No. 63/042,660, filed on Jun. 23, 2020.

(51) Int. Cl.
*A61B 17/30* (2006.01)

(52) U.S. Cl.
CPC ........ *A61B 17/30* (2013.01); *A61B 2017/301* (2013.01)

(58) Field of Classification Search
CPC ........ A61B 2017/301; A61B 2017/303; A61B 17/30; A61B 17/29; A61B 2017/2906; A61B 2017/2908; A61B 2017/2915; A61F 2/1664; A61F 9/00736; A61F 2/1662
USPC .......................................... 606/210; 294/99.2
See application file for complete search history.

(56) References Cited

U.S. PATENT DOCUMENTS

| | | | | |
|---|---|---|---|---|
| 5,501,698 | A * | 3/1996 | Roth | A61B 17/1285 606/174 |
| 6,083,223 | A * | 7/2000 | Baker | A61B 18/1445 606/49 |
| 9,987,071 | B2 * | 6/2018 | Van Tol | A61B 18/1206 |
| 2006/0074435 | A1 * | 4/2006 | Seil | A61F 2/1664 606/107 |
| 2009/0030424 | A1 * | 1/2009 | Tuli | A61F 2/1664 606/205 |
| 2016/0199082 | A1 * | 7/2016 | Batchelor | A61B 18/14 606/206 |
| 2016/0310155 | A1 * | 10/2016 | Kimura | A61B 17/29 |

* cited by examiner

*Primary Examiner* — Kathleen S Holwerda
*Assistant Examiner* — Serenity A Miller
(74) *Attorney, Agent, or Firm* — Michael Best & Friedrich LLP (57) ABSTRACT

The present disclosure describes a three-pronged forceps. The forceps are particularly useful for removing an intraocular lens from an eye.

13 Claims, 10 Drawing Sheets

FORCEPS

CROSS-REFERENCE TO RELATED APPLICATIONS

This application is a non-provisional of and claims the benefit of U.S. Provisional Patent Application No. 63/042,660, filed on Jun. 23, 2020, the contents of which are incorporated herein by reference.

FIELD

The present disclosure relates to a forceps for eye surgery.

BACKGROUND

It is a recognized goal in the medical arts to minimize trauma to a surgical site. Some of the ways to do this are to minimize the number of tools used, the size and number of incisions, and the total number of times tools must be inserted and removed. Among the benefits of minimizing invasiveness are faster healing, reduced operation duration, and shorter patient stays in medical facilities.

For example, in ophthalmology, doctors sometimes have to explant an intraocular lens (IOL) that was previously placed. Physicians often use a combination of two or more instruments simultaneously or use scissors to cut the lens prior to removal with a different tool. Patient outcomes may improve by decreasing the number of devices involved or minimizing the size of incisions for ophthalmic surgery.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure provides, in part, devices and methods for folding or removing objects during surgery.

In one aspect, the present disclosure provides a grasping device, comprising, consisting of, or consisting essentially of a first and a second prong that are substantially parallel to a plane and are able to be moved toward each other along the plane; a third prong situated between the first and second prongs that is able to be moved in a direction substantially perpendicularly to the plane; a proximal end to which the first, second, and third prongs connect; and a guide on the third prong that causes the third prong to move substantially perpendicular to the plane when the first and second prongs are moved toward each other.

In some embodiments, in an open position, the distal ends of the first and second prongs are spaced apart and the distal end of the third prong is positioned below the distal ends of the first and second prongs, and wherein in the closed position the spacing between the first and second prongs is reduced and the distal end of the third prong is positioned above the distal ends of the first and second prongs.

In some embodiments, a fold can be imparted in an object contacted by the prongs during movement from the open position to the closed position.

In some embodiments, the guide comprises a wedge shape, wherein substantially simultaneous pressure from the first prong on a first side of the wedge shape and pressure from the second prong on a second side of the wedge shape causes the wedge shape to move in a direction perpendicular to a third side of the wedge shape. In other embodiments, the guide comprises a plurality of curved surfaces.

In some embodiments, the distal ends of the first, second, and third prongs are disposed at an angle relative to the plane. In some embodiments, the angle is in a range of approximately 0-90°, 0-45°, or 10-45°.

In some embodiments, the distal ends have a textured surface, and in some embodiments the distal ends have bumps and/or grooves.

In some embodiments, a maximum distance between any two distal ends in the closed position is 2.7 millimeters.

Another aspect of the present disclosure provides methods of using the grasping device according to the present disclosure to fold an object (e.g., an IOL). In one embodiment, the method comprises, consists of, or consists essentially of positioning the first and second prongs over one side of the object; positioning the third prong over the opposite of side object; and squeezing the first and second prongs toward each other along the plane, thereby moving the third prong in a perpendicular direction between the first and second prongs and folding the object. Some embodiments use the device to fold and remove an IOL. In some embodiments, removal is through incisions no larger than 2.7 millimeters in length.

In another embodiment, a grasping device includes a first prong including a proximal end and a distal end, a second prong including a proximal end and a distal end, and a third prong including a proximal end and a distal end, the third prong being positioned between the first prong and the second prong. The proximal end of the first prong, the proximal end of the second prong, and the proximal end of the third prong are coupled to one another. The first prong and the second prong are movable substantially parallel to a first plane and, in response to movement of the first prong and the second prong, the third prong is movable substantially parallel to a second plane that is substantially perpendicular to the first plane.

In another embodiment, a grasping device includes a first prong including a proximal end and a distal end. An inner surface extends between the proximal end and the distal end, and an outer surface opposite the inner surface extends between the proximal end and the distal end. A second prong includes a proximal end and a distal end. An inner surface extends between the proximal end and the distal end, and an outer surface opposite the inner surface extends between the proximal end and the distal end. A third prong includes a proximal end and a distal end, and is positioned between the first prong and the second prong. The proximal end of the first prong, the proximal end of the second prong, and the proximal end of the third prong are coupled to one another, and the distal end of the first prong, the distal end of the second prong, and the distal end of the third prong are movable relative to one another between a first position and a second position. In the first position, the outer surface at the distal end of the first prong and the outer surface at the distal end of the second prong are spaced apart from one another by a first distance and the distal end of the third prong is positioned below the distal ends of the first prong and the second prong. In the second position, the outer surface at the distal end of the first prong and the outer surface at the distal end of the second prong are spaced apart from one another by a second distance that is smaller than the first distance and the distal end of the third prong is positioned above the distal ends of the first prong and the second prong.

In yet another embodiment, a method of removing an object from a cavity with a grasping device is disclosed. In this embodiment, the grasping device including a first prong including a proximal end and a distal end, a second prong including a proximal end and a distal end, and a third prong including a proximal end and a distal end, the third prong being positioned between the first and second prongs, wherein the proximal end of the first prong, the proximal end of the second prong, and the proximal end of the third prong are coupled to one another, and the distal end of the first prong, the distal end of the second prong, and the distal end of the third prongs are movable relative to one another. The method includes positioning the first prong and the second prong adjacent a first side of the object, positioning the third prong adjacent a second, opposite side of the object; and moving the first prong and the second prong toward each other substantially parallel to a first plane thereby causing the third prong to move substantially parallel to a second plane that is substantially perpendicular to the first plane to fold the object Other aspects of the invention will become apparent by consideration of the detailed description and accompanying drawings.

BRIEF DESCRIPTION OF THE DRAWINGS

The accompanying Figures and Examples are provided by way of illustration and not by way of limitation. The foregoing aspects and other features of the disclosure are explained in the following description, taken in connection with the accompanying example figures (also "FIG.") relating to one or more embodiments, in which.

DETAILED DESCRIPTION

Before any constructions of the invention are explained in detail, it is to be understood that the invention is not limited in its application to the details of construction and the arrangement of components set forth in the following description or illustrated in the following drawings. The disclosure is capable of other constructions and of being practiced or of being carried out in various ways.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. The methods and compositions disclosed herein can be used on a sample either in vitro (for example, on isolated cells or tissues) or in vivo in a subject (i.e. living organism, such as a patient). In some embodiments, the subject comprises a human who is undergoing eye treatment with a device as prescribed herein.

"Substantially" as used in the specification means an amount that is at least 80% or more than the specified orientation or relationship. For example, when a first element is indicated as being substantially parallel or substantially perpendicular to a second element, it means that the first element is 100% or completely parallel or perpendicular to the second element, but also includes a tolerance amount of 80% or more of the indicated orientation or relationship.

Unless otherwise defined, all technical terms used herein have the same meaning as commonly understood by one of ordinary skill in the art to which this disclosure belongs. It is sometimes necessary for ophthalmologists to remove intraocular lenses (IOL) that were previously placed. Currently, there are not task-specific devices to accomplish this. Rather, clinicians often use a combination of two random instruments or use scissors to cut the lens prior to removal. This increases the risk of injury to the eye.

The present disclosure provides a solution to these and other challenges using a unique set of forceps. The forceps include three prongs which are generally parallel to one another when viewed from opposite sides of the forceps, and which connect on one end. As the two outer prongs are squeezed together (e.g., horizontally), the central prong moves in a perpendicular (e.g., vertical) direction. This provides three gripping points for the forceps to clasp or close onto the IOL and causes the flexible IOL to fold within the grasp of the forceps. Hence, a small, controlled incision can be made in a cornea, through which the forceps are inserted and through which the IOL/forceps can then be extracted.

Figure 1:
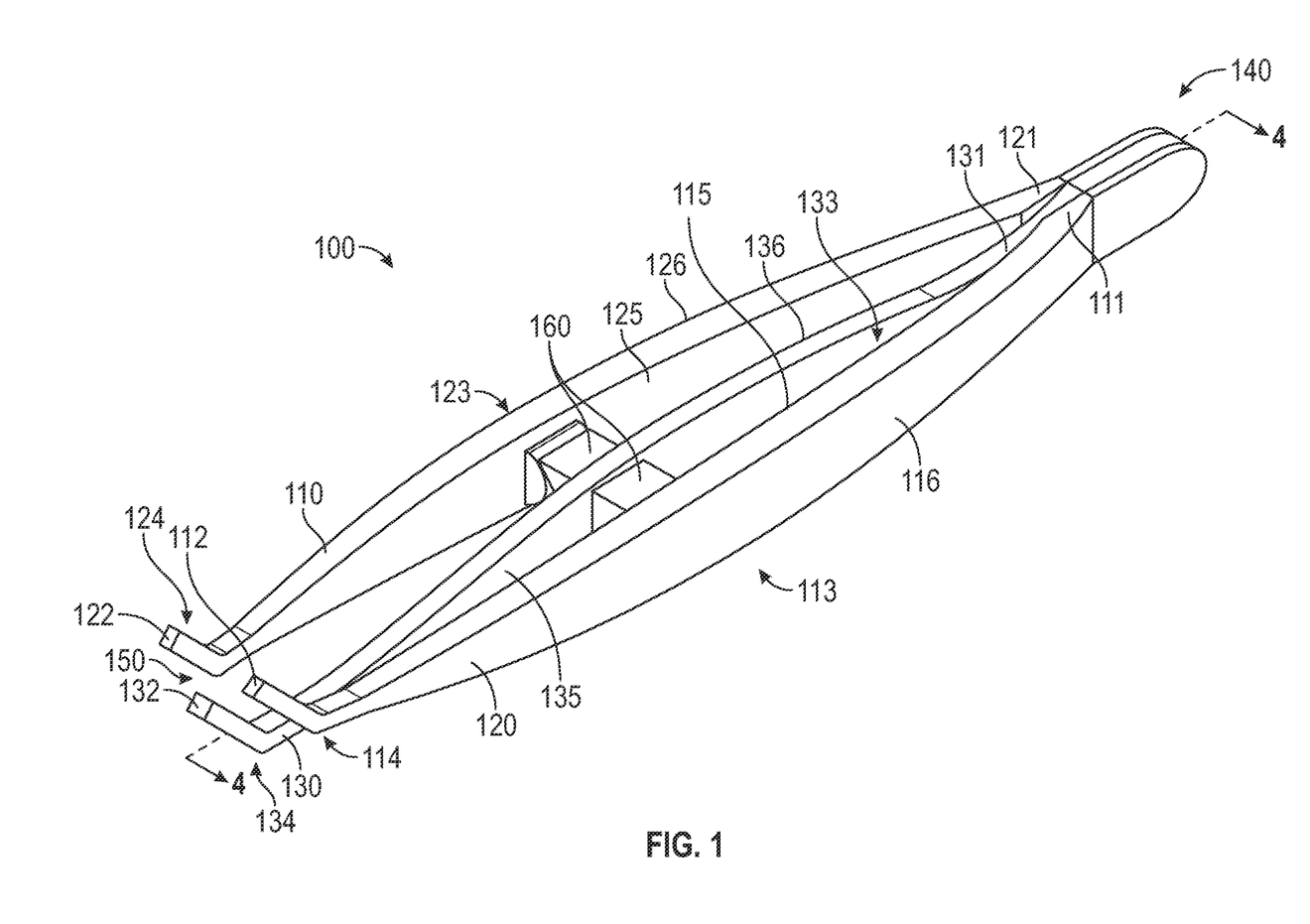
FIG. 1 is a perspective view of a forceps in accordance with one embodiment of the present disclosure.
Figure 2:
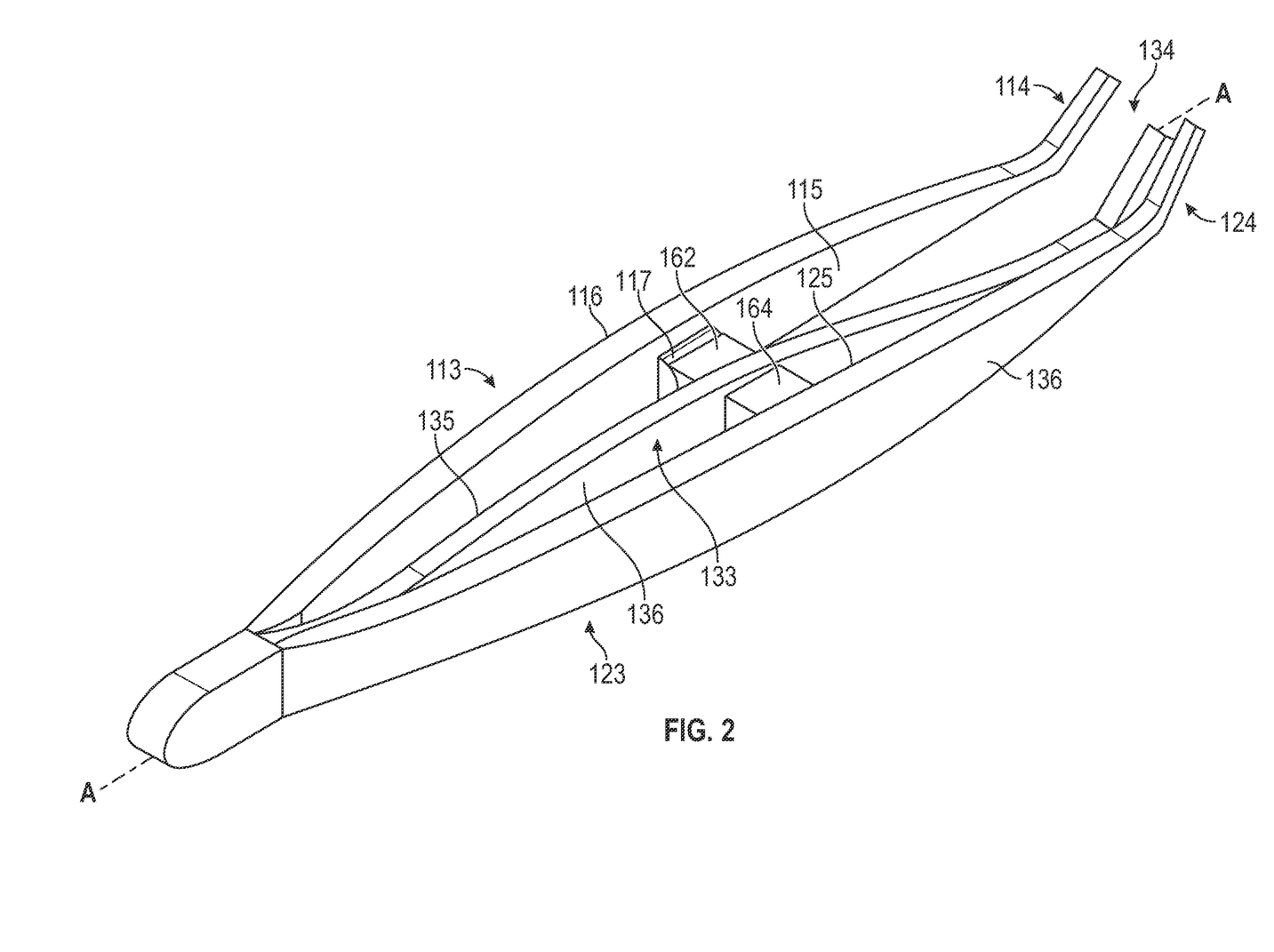
FIG. 2 is another perspective view of the forceps shown in FIG. 1.
Figure 3:
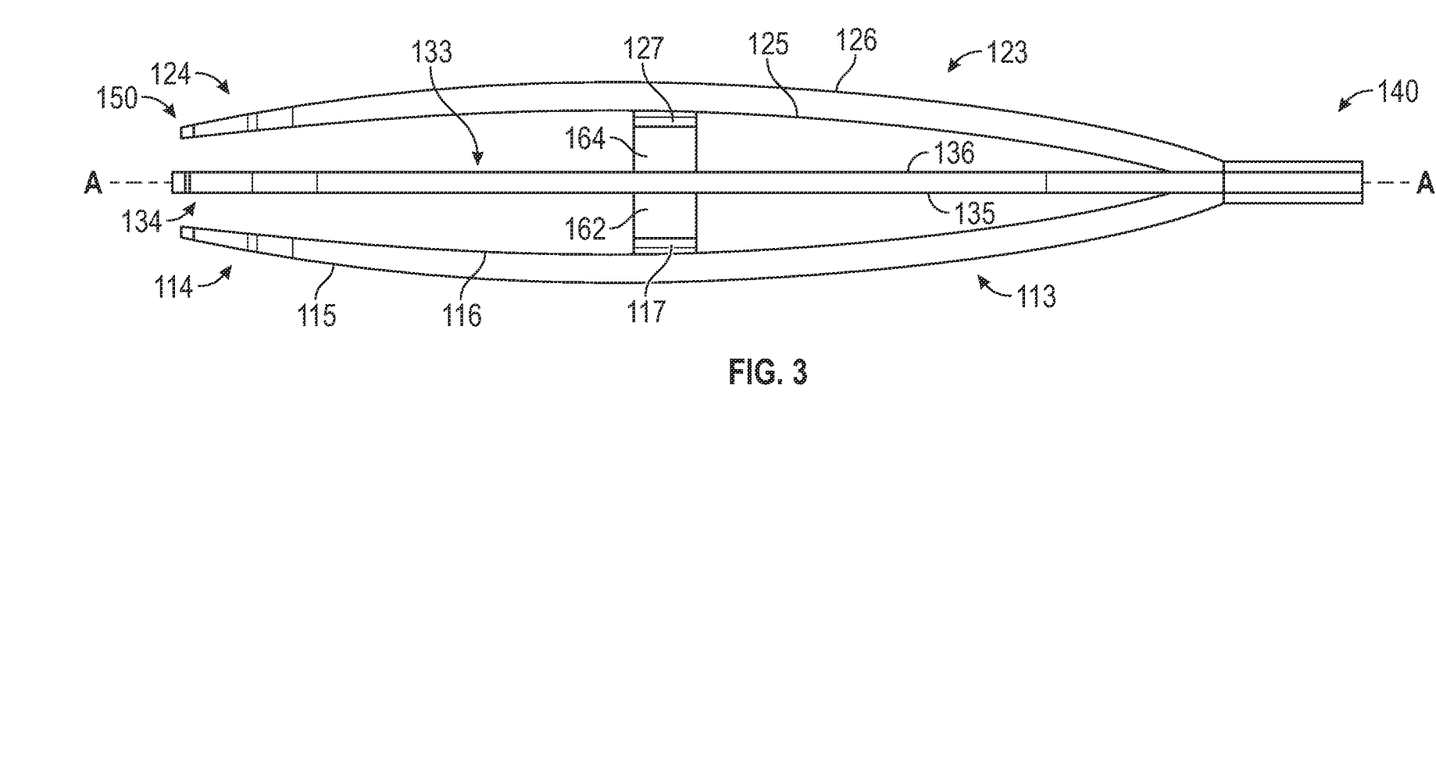
FIG. 3 is a top view of the forceps shown in FIG. 1.
Figure 4:
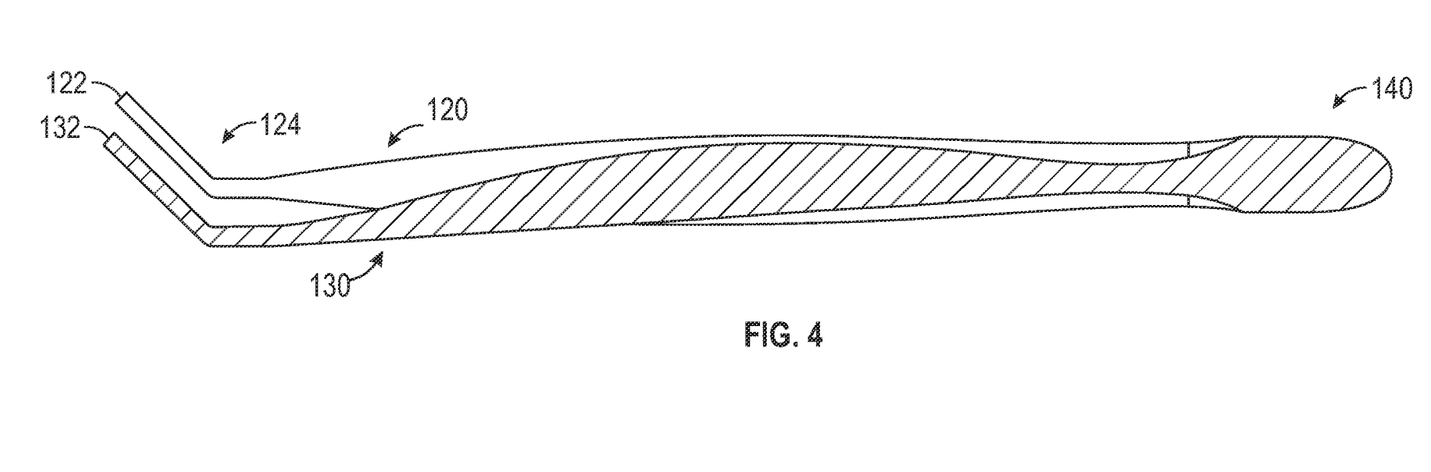
FIG. 4 is a cross-sectional view of the forceps shown in FIG. 1 along the line 4-4.
Figure 5:
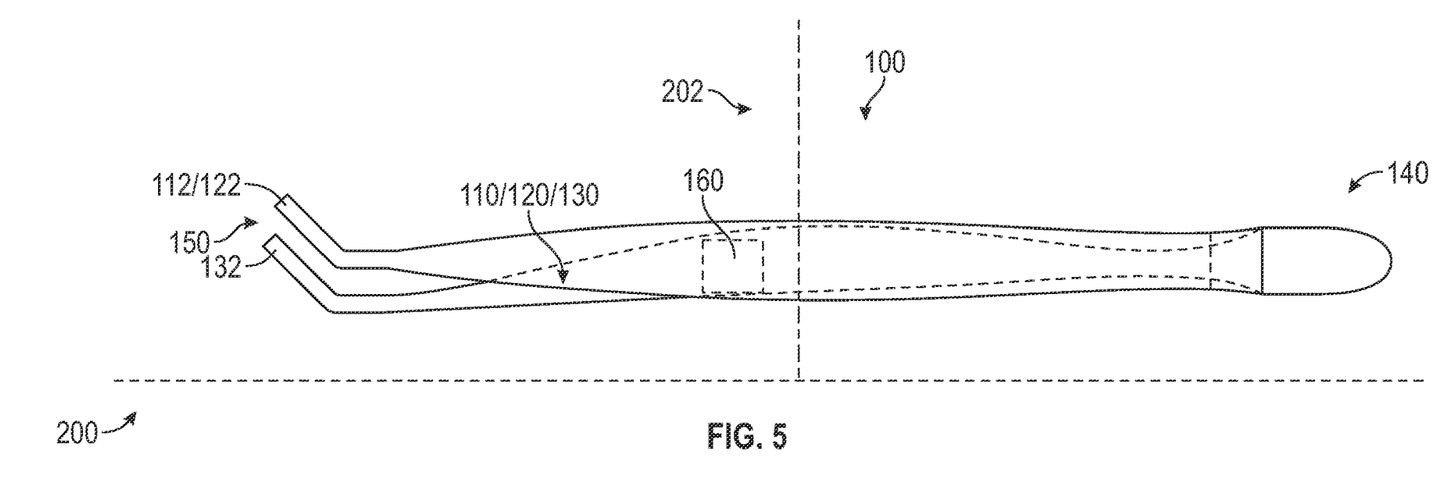
FIG. 5 is a side view of the forceps shown in FIG. 1.
Figure 6:
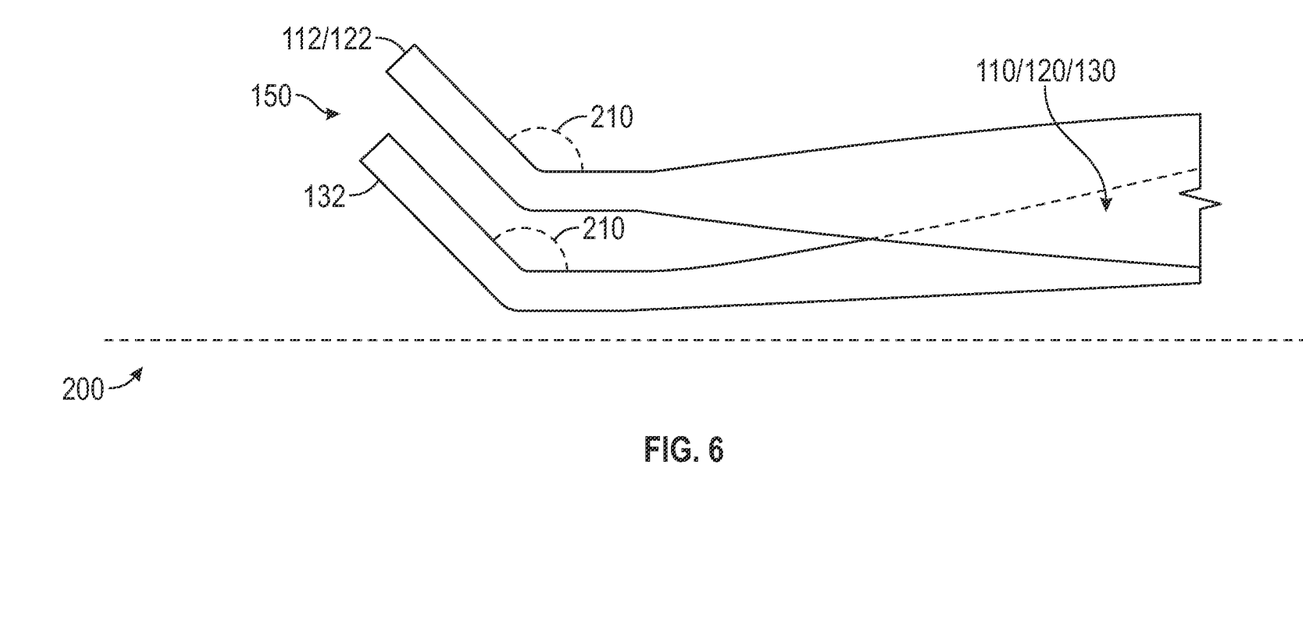
FIG. 6 is a detailed side view of the forceps shown in FIG. 1.
Figure 7:
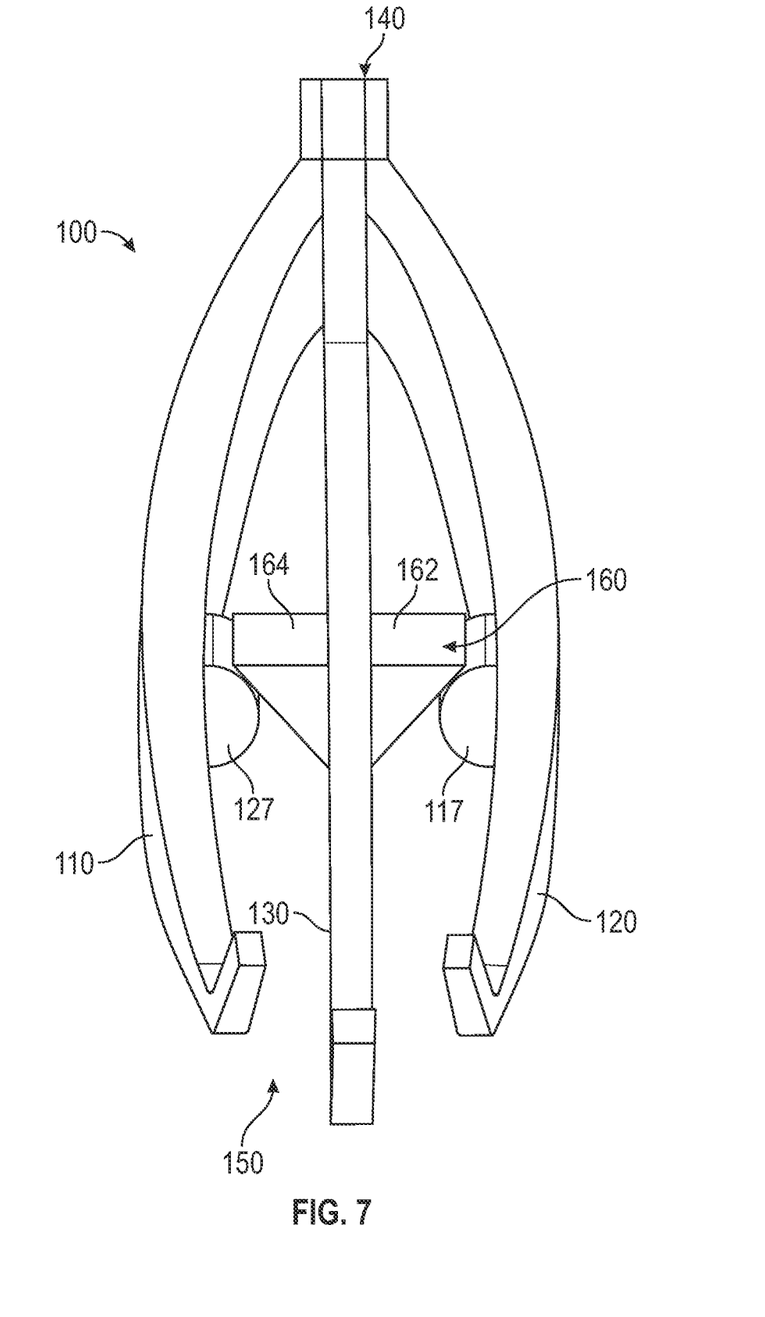
FIG. 7 is a detailed perspective view of the forceps shown in FIG. 1.
Figure 8:
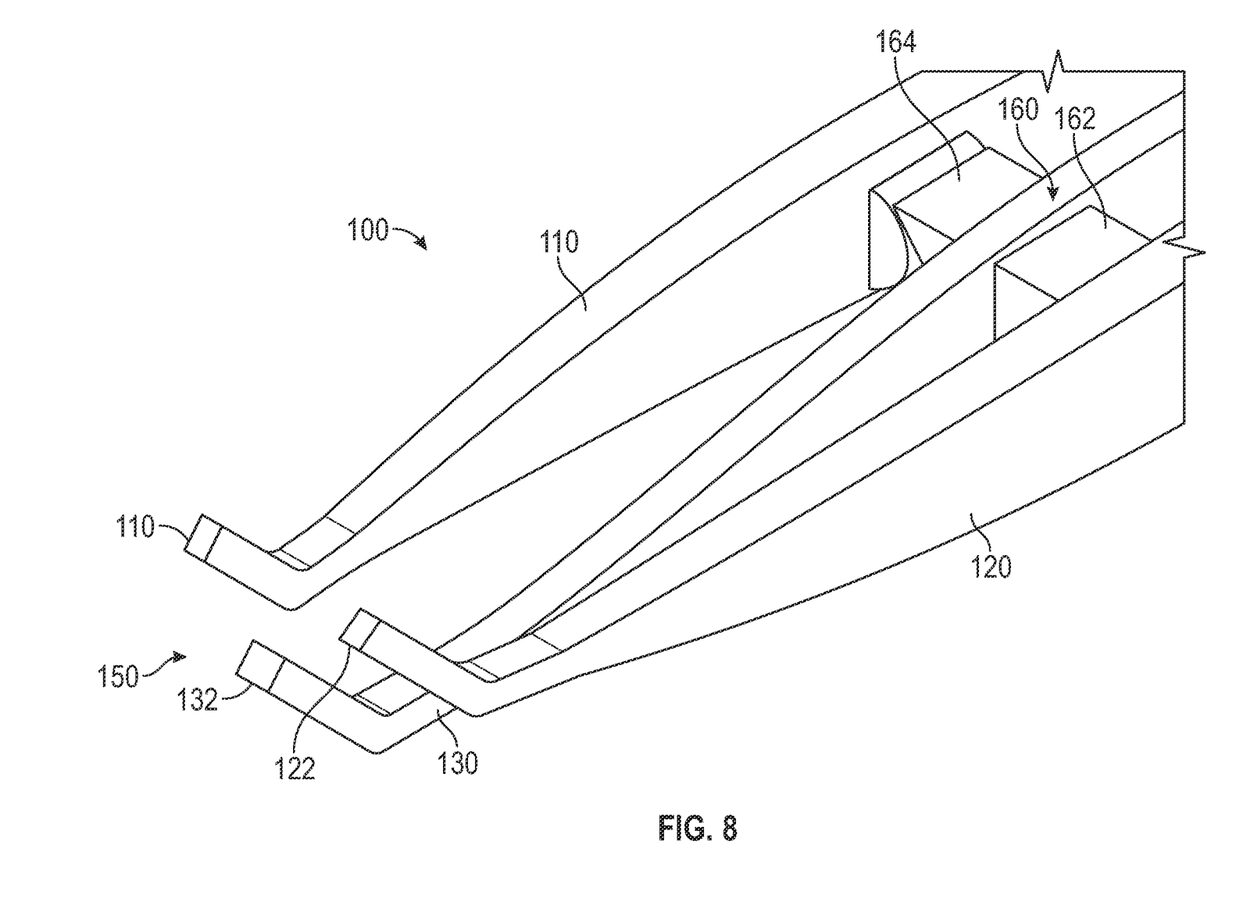
FIG. 8 is another detailed perspective view of the forceps shown in of FIG. 1.

Referring first to FIGS. 1-3, an embodiment of a grasping device or forceps in accordance with the present disclosure is illustrated, which has been designated generally by reference number 100. The grasping device 100 includes a first prong 110 and a second prong 120 that are substantially parallel to each other. The grasping device 100 also includes a third prong 130, situated or positioned between the first and second prongs 110/120. The three prongs are connected at a proximal end 140, and are separated at a distal end 150. A longitudinal axis A (FIGS. 2-3) of the grasping device 100 extends between the proximal end 140 and the distal end 150. A length of the grasping device 100 may have any suitable length (e.g., about 87 mm). Additionally, a maximum width of the grasping device 100 may be any suitable width (e.g., about 14.7 mm). Located on the third prong 130, there is illustrated a guide 160. The guide 160 enables the third prong 130 to move in a direction generally perpendicular to the directions of the first prong 110 and the second prong 120 when the first prong 110 and the second prong 120 are actuated (e.g., moved closer to one another). In practice, the user can move or squeeze the first prong 110 and the second prong 120 toward each other to move the third prong 160.

Illustrated in FIGS. 1, 5, 6, and 8 is a closer view of the prongs 110/120/130 in the example embodiment illustrated in FIG. 1. The first prong 110 has a proximal end 111 positioned at or adjacent to the proximal end 140 of the grasping device 100 and a distal end 112 opposite the proximal end 111 that is positioned at or adjacent to the distal end 150 of the grasping device 100. The second prong 120 has a proximal end 121 positioned at or adjacent to the proximal end 140 of the grasping device 100 and a distal end 122 opposite the proximal end 121 that is positioned at or adjacent to the distal end 150 of the grasping device 100.

The second prong 120 is essentially a mirror image of the first prong 110. Therefore, although the details of the first prong 110 are discussed in detail, it should be understood that the details apply to the second prong 120, as well. Accordingly, like structure is identified with like reference numerals plus "10." A body of the first prong 110 has a grasp or engagement portion 113 extending from the proximal end 111 towards the distal end 112 and an insertion portion 114 extending from the engagement portion 113 to the distal end 112. The engagement portion 123 is arcuately-shaped. The insertion portion 114 defines a length and is positioned at an angle 210 relative to the engagement portion 113. The first prong 110 defines an inner surface 115 that is positioned adjacent the third prong 130 and an outer surface 116 that is opposite the inner surface 115. In the illustrated embodiment, the inner surface 125 of the engagement portion 113 is generally concave and the outer surface 116 of the engagement portion 115 is generally convex. As will be discussed in greater detail below a projection 117 (e.g., a first guide) extends from the inner surface towards the longitudinal axis A and the third prong 130. Generally, and with respect to FIG. 5, the engagement portions 113 adjacent the proximal end 111 is positioned at a location that is substantially coincident with a location of the engagement portion 113 adjacent the distal end 112. That is, a line drawn between the location of the engagement portion 113 adjacent the proximal end 111 and the location of the engagement portion 113 adjacent to the distal end 112 is generally parallel to a first plane 200.

Further with respect to FIGS. 1, 5, 6, and 8, the third prong 130 runs generally along the longitudinal axis A, A second plane 202 (FIG. 5) is defined along the longitudinal axis A and through the third prong 130, The second plane 202 is perpendicular to the first plane 200. The third prong 130 has a proximal end 131 positioned at the proximal end 140 of the grasping device 100 and a distal end 132 opposite the proximal end 131 and positioned at the distal end 150 of the grasping device 100. A body of the third prong 130 has a guide portion 133 extending from the proximal end 131 towards the distal end 132 and an insertion portion 134 extending from the guide portion 133 to the distal end 132. The guide portion 133 includes a first surface 135 that is positioned adjacent the first prong 110 and a second surface 136 that is opposite the first surface 135 and adjacent the second prong 120. The insertion portion 134 defines a length and is positioned at an angle 210 relative to the guide portion 130. As will be discussed in greater detail below a projection 162 (e.g., a second guide) extends from the first surface 135 towards the first prong 110 and a projection 164 (e.g., a second guide) extends from the second surface 136 towards the second prong 120. Generally, and with respect to FIG. 5, the guide portion 133 of the third prong 130 adjacent the distal end 132 is positioned at a location below a location of the guide portion 130 adjacent the proximal end 131. That is, a line drawn between the location of the guide portion 133 adjacent the proximal end 131 and the location of the guide portion 133 adjacent to the distal end 132 generally slopes towards the first plane 200 (e.g., downward), Accordingly, in the illustrated embodiment, two of the three prongs 110/120 are generally parallel to the plane 200, while the third prong 130 is positioned at a non-parallel angle (e.g., an acute angle) relative to the plane 200. In other embodiments, all three prongs 110/120/130 may be substantially parallel to the plane 200.

Figure 9:
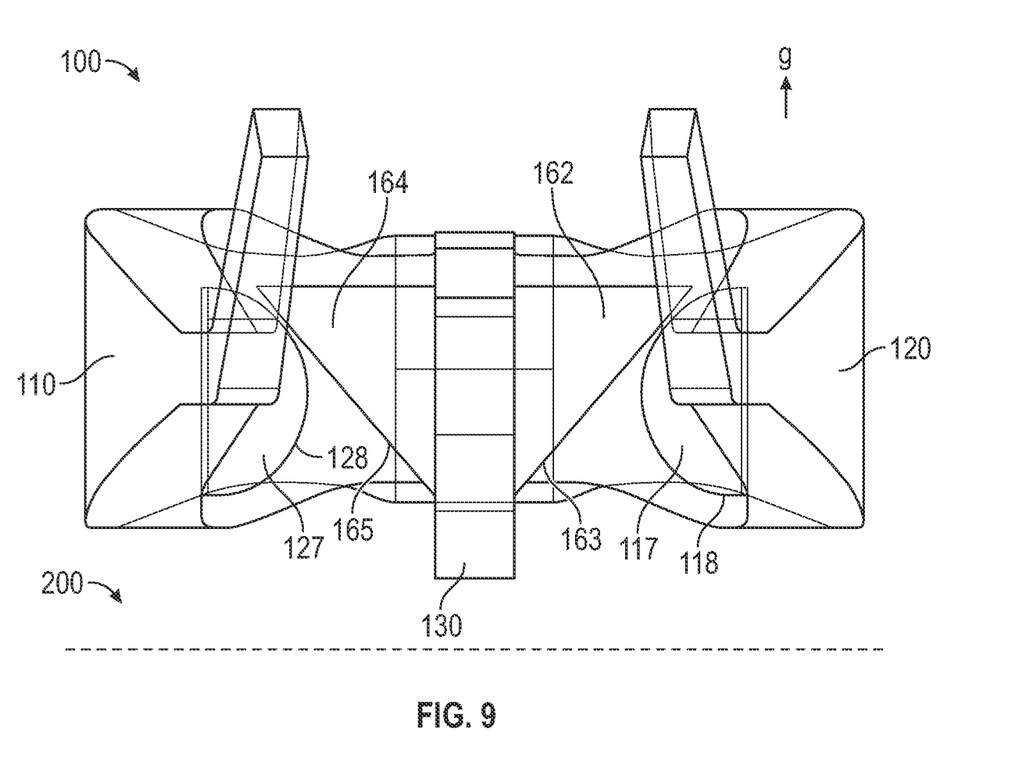
FIG. 9 is a front view of the forceps of FIG. 1.

The first, second, and third prongs 110/120/130 are movable between in an open position (e.g. a first position) and a closed position (e.g., a second position). In the open position, the outer surfaces 116/126 of the insertion portions 114/124 of the first and second prongs 110/120 are spaced apart from one another by a first distance and the insertion portions 134 of the third prong 130 is positioned below the insertion portions 114/124 of the first and second prongs 110/120, respectively. In the closed position, the outer surfaces 116/126 of the insertion portions 114/124 of the first and second prongs 110/120 are spaced apart from one another by a second distance and the insertion portion 134 of the third prong 130 is above the insertion portions 114/124 of the first and second prongs 110/120. The second distance is smaller than the first distance. In some embodiments, the second distance is preferably less than about 3 mm. In some embodiments, the second distance is preferably no greater than about 2.7 mm. In some embodiments, the second distance may be about 2.2 mm. As noted above, when moving between the open and closed positions, the first and second prongs 110/120 move generally horizontally, while the third prong 130 moves generally vertically. In some embodiments, the third prong 130 may move along a generally perpendicular trajectory relative to the first plane 200. In other embodiments, the third prong 130 may move along a arcuate trajectory relative to the first plane 200. In one example embodiment, the guide 160 generally has a wedge shape. In the example embodiment of FIGS. 1-3 and 7-9, the guide includes the first projection 162 on the third prong 130 that contacts the corresponding first projection 117 on the first prong 110 and the second projection 164 on the third prong 130 that contacts the corresponding second projection 127 on the second prong 120. In the illustrated embodiments, together, the projections 162/164 define a wedge shape when viewed from the distal end 150 of the grasping device 100. Moreover, with respect to FIG. 9, each of the projections 162/164 define a linear surface 163/165 that is generally oriented at a non-parallel angle (e.g., an acute angle) relative to the second plane 202. Moreover, in the illustrated embodiment, each of the projections 117/127 is hemispherically-shaped and defines an arcuately shaped (e.g., curved) surface 118/128. The guide 160 may have any suitable height (e.g., about 3.9 mm), but is generally smaller than a maximum height (e.g., about 5 mm) defined by the first and second prongs 110/120.

When a user imparts a force in the directions of arrows F (FIG. 10B) on each of the first and second prongs 110/120 (e.g., the engagement portions 113, 123 of the first and second prongs 110/120) in a direction towards the longitudinal axis A, the first and second prongs 110/120 approximate and therefore move from the open position to the closed position. Accordingly, the surfaces 118/128 of the respective projections 117/127 move or slide along the surfaces 163/165 of the respective projections 162/164, causing the third prong 130 to move in a first direction (e.g., in the direction of arrow G) from the open position to the closed position. The arrow G is generally illustrated as having a trajectory perpendicular to the first plane 200 in the illustrated embodiment, but, as noted above, in some embodiments, the arrow G may have an arcuate trajectory. When the user releases the force on each of the first and second prongs 110/120 (e.g., the engagement portions 113, 123 of the first and second prongs 110/120), the first and second prongs 110/120 move away from one another and therefore move from the closed position to the open position. Accordingly, the surfaces 118/128 of the respective projections 117/127 move or slide along the surfaces 163/165 of the respective projections 162/164, causing the third prong 130 to move a second direction opposite the first direction (e.g., in the direction opposite of the arrow G) from the closed position to the open position.

As will be discussed in greater detail below, the grasping device 100 is well-suited for removing and/or grasping objects during surgical procedures. As such, in practice, the distal end 150 may be inserted at various angles depending on the object to be grasped. Thus, it is advantageous that the insertion portions 114/124/134 are curved and/or disposed at various angles. In the illustrated embodiment, the insertion length of each the insertion portions 114/124/134 measures about 6 mm, but in other embodiments, the insertion length may measure about 3 mm to about 7 mm. In some embodiments, the insertion lengths of the first and second prongs 110/120 may be shorter or longer than the insertion length of the third prong 130. For example, the insertion lengths of the first and second prongs 110/120 may be about 5.6 mm, for example, and the insertion length of the third prong 130 may be about 7.1 mm, for example. In the illustrated embodiment, the angle of each of the insertion portions measures about 135 degrees, but in other embodiments the angle may be measure 0 degrees to 180 degrees. Additionally, the angle 210 of the first and second prongs 110/120 may be greater or less than the angle 210 of the third prong 130. Moreover, as will be discussed in greater detail below, a thickness of the insertion portions (between the inner and outer surfaces) is preferably as small as possible while also maintaining an appropriate strength.

Biocompatibility with the eye and/or other parts of the body are key to surgical success. Hence, device 100 can be made of any suitable biocompatible material, such as stainless steel, nitinol, biocompatible plastics, etc. Preferably, the biocompatible material may also be sterilizable.

In the illustrated embodiment, the grasping device 100 is integrally formed as a unitary element from a single sterilizable material. Therefore, the proximal ends 111/121/131 are coupled to one another during the forming process (e.g., 3D printing, molding, or any other suitable process). In the illustrate embodiment, a thickness of the third prong 130 is smaller than a maximum thickness of each of the first and second prongs 110/120. For example, the thickness of the third prong 130 is about 1.5 mm, while the maximum thickness of each of the first and second prongs 110/120 is greater than about 1.5 mm. The third prong 120 has a uniform thickness along its length in the illustrated embodiment, although it may have a variable thickness in other embodiments. Despite the greater maximum thickness of the first and second prongs 110/120, a thickness of the insertion portions 114/124 of each of the first and second prongs 110/120 is less than the maximum thickness. For example, in the illustrated embodiment, the thickness of each of the insertion portions of each of the first and second prongs 110/120 is about 0.87 mm. Without being bound by a single theory, it is believed that constructing the third prong 130 to have a smaller thickness than the maximum thickness of the first and second prongs 110/120 may help the third prong 130 move parallel to the second plane 202 between the open and closed positions.

In other embodiments, the grasping device may be formed in other ways. For example, the first and second prongs 110/120 may be integrally formed with a material and the third prong 130 may be integrally formed of a material. The materials of the first and second prongs 110/120 may be the same (e.g., have the same mechanical properties) or different (e.g., have different mechanical properties). The third prong 130 may be separately coupled to the first and second prongs 110/120. That is, for example, the proximal end 131 of the third prong 130 may be movably (e.g., pivotably, hingably, rotatably) coupled to the proximal end 140 of the grasping device 100 (and therefore the proximal ends 111/121 of the first and second prongs 110/120). In one, non-limiting example, the proximal end 131 of the third prong 130 may be coupled to the proximal ends 111/121 of the first and second prongs 110/120 by a pin or fastener that extends substantially perpendicular or transverse to the longitudinal axis A.

Figure 10A:
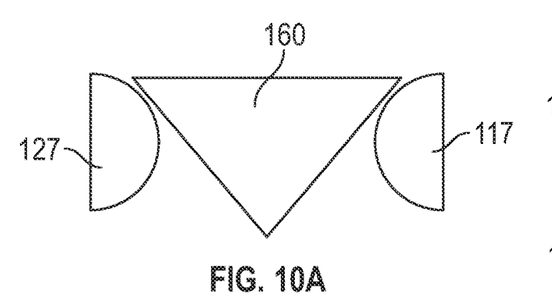
FIG. 10A is a schematic illustration of the forceps shown in FIG. 1 in an open position.
Figure 10B:
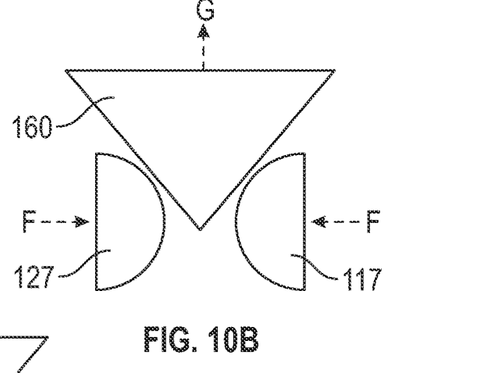
FIG. 10B is a schematic illustration of the forceps shown in FIG. 1 in an intermediate position.
Figure 10C:
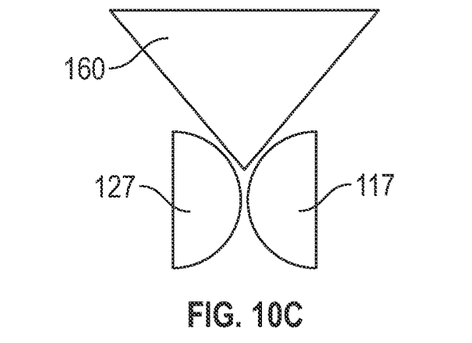
FIG. 10C is a schematic illustration of the forceps shown FIG. 1 in a closed position.

In practice, a user can move or squeeze the device 100, pushing prongs one and two 110/120 toward each other in order to grasp an object. This moves the device 100 from the open to the closed position, as discussed above. FIGS. 10A through IOC illustrate the functionality of a wedge-shaped guide 160 interacting with the projections 117/127 when the grasping device 100 is moved from the open position to the closed position. FIG. 10A illustrates the open position, FIG. 10B illustrates an intermediate position, and FIG. 10C illustrates the closed position. Arrows in FIG. 10B illustrate the direction of movement of the relevant structures when the grasping device 100 is closing. Starting from the open position, as prongs one and two 110/120 are squeezed toward each other (in the direction of arrows F), the surfaces 118/128 of the projections 117/127 on prongs one and two 110/120 exert force on the surfaces 163/165 of the guide 160. This force causes the guide 160 to move in the direction of arrow G, which is in a direction generally perpendicular to the movement of the projections 117/127. As the projections 117/127 approximate, the forces exerted on the surfaces 163/165 of the guide 160 causes the guide 160 to move perpendicularly to a third side.

Similar functionality can be generated by using wedge-shaped projections 117/127 and/or a plurality of curved surfaces on the guide 160.

The grasping device 100 is well-suited for grasping objects during surgery, some of which may be slippery. Thus, in some embodiments, some or all of the distal ends 112/122/132 of the prongs 110/120/130 have a textured surface. In some embodiments the distal ends 112/122/132 have a plurality of bumps and/or grooves. This textured surface, bumps, and/or grooves could be located between the location of the angles 210 and the most distal portion of the distal ends 112/122/132.

In another aspect of the present disclosure, a method of removing an IOL with the disclosed forceps is provided. In an example method, a small incision is initially made in a cornea. For example, a typical incision for cataract and IOL surgery is about 2.7 mm. In a first step, the center prong slides under IOL that resides in the anterior chamber of the eye. The outer prongs then slide over the IOL. The forceps are then closed, and the center prong starts to move superiorly ("up") between the other two prongs in order to cause a fold of the IOL (leading to the lens being folded in half). The lens can then be removed through the incision.

Figure 11A:
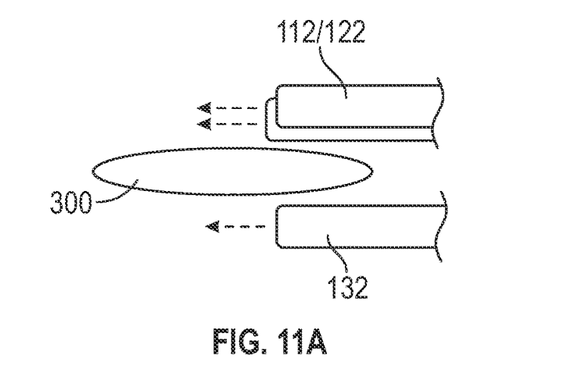
FIG. 11A is a schematic illustration of the forceps of FIG. 1 shown in an open position, as viewed from a side of the forceps.
Figure 11B:
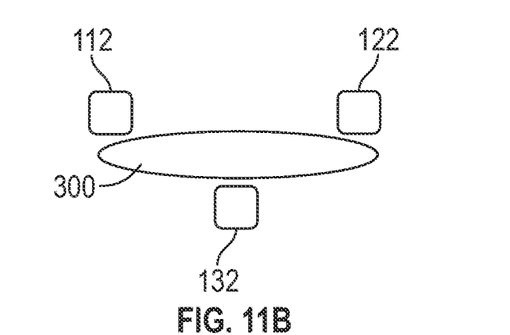
FIG. 11B is a schematic illustration of the forceps shown in FIG. 1 in an open position, as viewed from a front of the forceps.
Figure 11C:
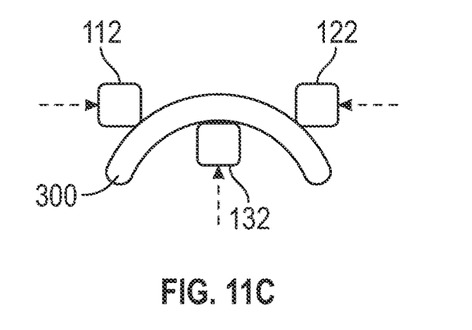
FIG. 11C is a schematic illustration of the forceps shown in FIG. 1 in a closed position, as viewed from a side of the forceps.
Figure 11D:
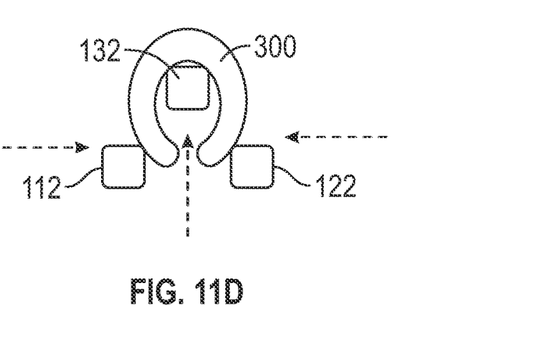
FIG. 11D is a schematic illustration of the forceps shown in FIG. 1 in a closed position, as viewed from a front of the forceps.

FIGS. 11A through 11D illustrate this method in further detail using the example grasping device 100. In FIG. 11A, the distal ends of the first and second prongs are positioned on one side of an object 300, while the distal end 132 of the third prong 130 is positioned on the opposite side of the object 300. FIG. 11B illustrates the resulting position. FIG. 11C illustrates the start of movement of the grasping device 100 from the open to the closed position. The distal ends of prongs one and two 112/122 move inward toward each other, which forces the distal end of prong three 132 upward in a perpendicular direction. This starts to create a bend in the object 300. As FIG. 11D illustrates, as the distal ends of prongs one and two 112/122 continue to approximate, the distal end of the third prong 132 moves upward between the first and second prongs 112/122. This ends with the distal end 132 above the first and second prongs 112/122, and results in a fold in the object 300.

In some embodiments, the object 300 is an intraocular lens, or IOL. By folding the IOL, the grasping device 100 can remove the IOL through an incision smaller than otherwise feasible. In some cases, the incision may be smaller in width than the original width of the IOL. In a non-limiting example, incision lengths can range from approximately 0.5 mm to 4 mm. One common size incision currently used by surgeons is 2.7 millimeters, and some embodiments enable the folded IOL to be removed through this size incision without cutting the IOL and removing in separate pieces and without inserting additional tools into the eye. This enables minimally invasive surgery thereby improves patient outcomes.

Often in surgical procedures, tissue needs to be held in place while inserting sutures, making incisions, or otherwise manipulating surrounding structures. Thus, in other embodiments, the object 300 is a piece of tissue, and the grasping device 100 can be used to hold it in place during a surgical procedure. The grasping device 100 can also be used to fold and thereby obstruct flow in small tubes.

Another aspect of the present disclosure provides all that is described and illustrated herein.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

Various features and advantages of the invention are set forth in the following claims.

What is claimed is:

1. A grasping device, comprising: a first prong including a proximal end, a distal end, an inner surface extending between the proximal end and the distal end, and an outer surface opposite the inner surface and extending between the proximal end and the distal end; a second prong including a proximal end, a distal end, an inner surface extending between the proximal end and the distal end of the second prong, and an outer surface opposite the inner surface of the second prong and extending between the proximal end and the distal end of the second prong; a third prong including a proximal end and a distal end, the third prong being positioned between the first prong and the second prong; a first guide coupled to the first prong; a second guide coupled to the second prong; and a third guide coupled to the third prong, wherein the proximal end of the first prong, the proximal end of the second prong, and the proximal end of the third prong are coupled to one another, and wherein the distal end of the first prong, the distal end of the second prong, and the distal end of the third prong are movable relative to one another between a first position and a second position, wherein in the first position, the outer surface at the distal end of the first prong and the outer surface at the distal end of the second prong are spaced apart from one another by a first distance and the distal end of the third prong is positioned below the distal ends of the first prong and the second prong; and wherein in the second position, the outer surface at the distal end of the first prong and the outer surface at the distal end of the second prong are spaced apart from one another by a second distance that is smaller than the first distance and the distal end of the third prong is positioned above the distal ends of the first prong and the second prong wherein when the first prong and the second prong move between the first position to the second position, the third guide on the third prong moves along the first guide and the second guide to move the third prong between the first position and the second position.

2. The grasping device of claim 1, wherein the first prong and the second prong are movable substantially parallel to a first plane between the first position and the second position and wherein the third prong is movable substantially parallel to a second plane between the first position and the second position, the second plane being substantially perpendicular to the first plane.

3. The grasping device of claim 1, wherein the second distance is about 3 mm or less.

4. The grasping device of claim 1, wherein the third guide coupled to the third prong includes a first linear surface and a second linear surface, and wherein the first guide includes an arcuate surface and the second guide includes an arcuate surface.

5. The grasping device of claim 1, wherein each of the first prong, the second prong, and the third prong include
a first portion extending from the proximal end towards the distal end, and
a second portion that extends from the first portion to the distal end, the second portion being an insertion portion, the insertion portion being positioned at an angle relative to the first portion.

6. The grasping device of claim 5, wherein the angle is greater than ninety degrees.

7. The grasping device of claim 5, wherein each of the insertion portions include a length between about 5 mm and 7 mm.

8. The grasping device of claim 7, wherein the length of the insertion portion of the first and second prongs is less than the length of the insertion portion of the third prong.

9. The grasping device of claim 1, wherein the distal end of the first prong, the distal end of the second prong, and the distal end of the third prong comprise a textured surface.

10. A method of removing an object from a cavity with the grasping device of claim 1, the method comprising:
positioning the first and second prongs adjacent a first side of the object;
positioning the third prong adjacent a second, opposite side of the object; and
moving the first and second prongs toward each other to fold the object.

11. The method of claim 10, wherein the object is an intraocular lens of the eye.

12. The method of claim 10, wherein moving the first prong and the second prong toward each other includes moving the first prong and the second prong toward each other such that a distance between the outer surface of the distal end of the first prong and the outer surface of the distal end of the second prong is less than about 3 mm.

13. The method of claim 10, wherein moving the first prong and the second prong toward each other includes moving the first prong and the second prong toward each other such that a distance between the outer surface of the distal end of the first prong and the outer surface of the distal end of the second prong is no greater than 2.7 millimeters in length.

* * * * *